(12) United States Patent
MacDougall et al.

(10) Patent No.: US 10,076,189 B2
(45) Date of Patent: Sep. 18, 2018

(54) ATTACHABLE HEADREST WITH EYE COVER

(71) Applicants: Alejandra Mariah MacDougall, Downey, CA (US); Matthew Lawrence Pacheco, Downey, CA (US); Michelle Tulean, Downey, CA (US); Glenn Yuji Yamasaki, Laguna Hills, CA (US)

(72) Inventors: Alejandra Mariah MacDougall, Downey, CA (US); Matthew Lawrence Pacheco, Downey, CA (US); Michelle Tulean, Downey, CA (US); Glenn Yuji Yamasaki, Laguna Hills, CA (US)

( * ) Notice: Subject to any disclaimer, the term of this patent is extended or adjusted under 35 U.S.C. 154(b) by 0 days.

(21) Appl. No.: 14/206,773

(22) Filed: Mar. 12, 2014

(65) Prior Publication Data

US 2015/0257538 A1    Sep. 17, 2015

(51) Int. Cl.
*A47C 7/38* (2006.01)
*A61F 9/04* (2006.01)
*B60N 2/882* (2018.01)
*B60N 2/48* (2006.01)

(52) U.S. Cl.
CPC ............... *A47C 7/383* (2013.01); *A61F 9/04* (2013.01); *B60N 2/4879* (2013.01); *B60N 2/882* (2018.02)

(58) Field of Classification Search
CPC ..... A47C 7/383; B60N 2/4879; B60N 2/4885
See application file for complete search history.

(56) References Cited

U.S. PATENT DOCUMENTS

| | | | |
|---|---|---|---|
| 4,679,263 A * | 7/1987 | Honer | 5/640 |
| 6,088,836 A * | 7/2000 | de Cordova | 2/171 |
| 6,607,245 B1 * | 8/2003 | Scher | 297/393 |
| 7,628,456 B1 * | 12/2009 | Swartz | 297/464 |
| 2002/0067063 A1 * | 6/2002 | Taborro | 297/397 |
| 2010/0237677 A1 * | 9/2010 | Nam | A47C 7/38 297/410 |
| 2011/0271421 A1 * | 11/2011 | Vahey | 2/173 |
| 2013/0312192 A1 * | 11/2013 | Lee | 5/639 |

* cited by examiner

*Primary Examiner* — Philip F Gabler
(74) *Attorney, Agent, or Firm* — Arent Fox LLP

(57) ABSTRACT

Various apparatuses are disclosed. An apparatus may include a headrest configured to accommodate a head of a user, and an eye cover connected to the headrest and configured to cover eyes of the user. The apparatus may also include headrest straps connected to the headrest and configured to adjustably fasten the headrest to a seat. The headrest straps may adjustably fasten the headrest to the seat by wrapping around the seat. The headrest may include a wedged portion that contacts a shoulder of the user. The headrest may include an indentation shaped substantially similar to at least a portion of the head of the user. The head of the user may be substantially immobilized when the headrest is fastened to a seat and the eye cover is fastened over eyes of the user.

19 Claims, 5 Drawing Sheets

ATTACHABLE HEADREST WITH EYE COVER

BACKGROUND

Field

The present disclosure relates, generally, to an apparatus and, more specifically, to an attachable headrest with an eye cover.

Background

A headrest may provide a user with neck and head support during times of rest. In some circumstances, the headrest may be used while the user is sitting upright. For example, the user may be sitting on a seat while traveling (e.g., on a seat while traveling in an airplane or bus). If the user falls asleep while sitting upright, the user's head may deviate from the headrest. For example, the user's head may move to the left, right, or forward such that their head is no longer supported by the headrest. Further, as the user's head moves, left, right, or forward, the headrest may also move because the headrest is no longer secured in place by the weight or force from the user's head. Accordingly, certain problems may exist in existing designs of headrests.

An eye cover may block substantial amounts of light while the user is resting. However, existing eye covers may not help to prevent movement of the user's head during times of rest. Accordingly, the problems described supra with respect to movement of the user's head during times of rest may not be overcome by existing eye covers. Therefore, a need exists for an attachable headrest with eye cover that reduces movement of the user's head during times of rest.

SUMMARY

One aspect of an apparatus is disclosed. An apparatus may include a headrest configured to accommodate a head of a user and attach to a seat, and an eye cover connected to the headrest and configured to cover eyes of the user, wherein the headrest and eye cover are collectively configured to limit movement of the head of the user.

Another aspect of an apparatus is disclosed. An apparatus may include means for accommodating a head of a user and attaching to a seat, and means for covering eyes of the user, wherein the means for covering eyes is connected to the means for accommodating, wherein the means for accommodating and means for covering eyes are collectively configured to restrain movement of the head of the user.

It is understood that other aspects of apparatuses will become readily apparent to those skilled in the art from the following detailed description, wherein various aspects of apparatuses are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses will now be presented in the detailed description by way of example, and not by way of limitation, with reference to the accompanying drawings, wherein.

DETAILED DESCRIPTION

Figure 1:
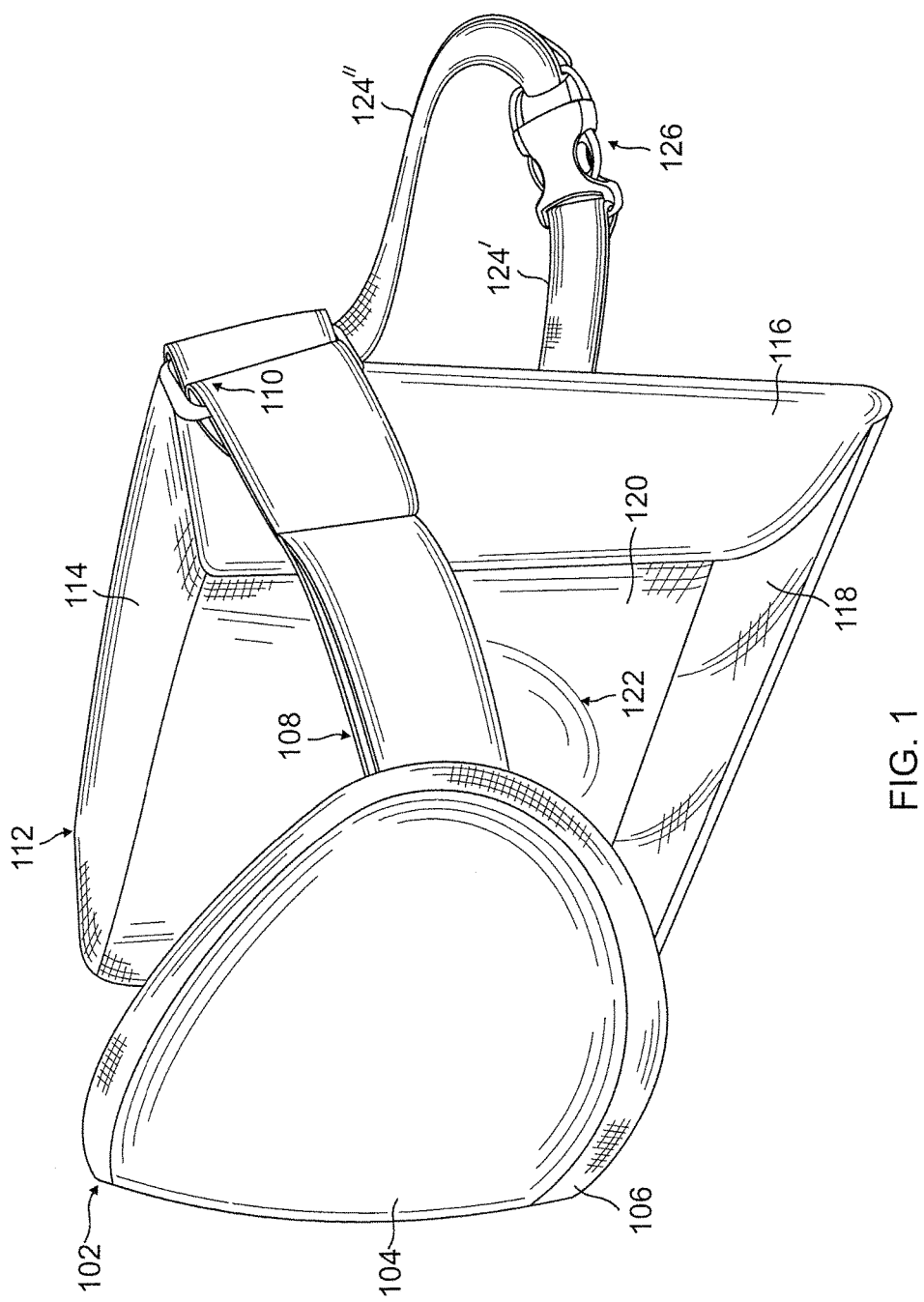
FIG. 1 is a diagram illustrating a side perspective view of an example of an attachable headrest with eye cover.

Various aspects of the disclosure will be described more fully hereinafter with reference to the accompanying drawings. This disclosure may, however, be embodied in many different forms by those skilled in the art and should not be construed as limited to any specific structure or function presented herein. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of this disclosure, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure and/or functionality in addition to or instead of other aspects of this disclosure. It should be understood that any aspect of the disclosure disclosed herein may be embodied by one or more elements of a claim.

Although particular aspects will be described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different circuits, technologies, systems, networks, and methods, some of which are illustrated by way of example in the drawings and in the following description. The detailed description and drawings are merely illustrative of the disclosure rather than limiting, the scope of the disclosure being defined by the appended claims and equivalents thereof.

FIG. 1 is a diagram illustrating a side perspective view of an example of an attachable headrest 112 with eye cover 102. The headrest 112 may be formed from a material that is sufficiently rigid to form the shape of the headrest 112 but sufficiently soft and malleable to provide comfort to the user. For example, the material forming the headrest 112 may be foam, memory foam, cotton, fabric, polyfil, pellets, microbeads, beanbag filler, feathers, polyester, plastic, wool, rubber, buckwheat, seeds, herbs, any combination of any one or more of the foregoing, and/or any other material suitable for forming the headrest 112. If the headrest 112 is an inflatable headrest, the material forming at least a portion of the headrest 112 may be air.

The headrest 112 may have a top portion 114, a bottom portion 118, side portions 116, and a front portion 120. The front portion 120 of the headrest 112 may be configured to accommodate a head of a user. For example, an indentation 122 in the front portion 120 of the headrest 112 may be shaped substantially similar to at least a portion of the head of the user. Accordingly, the head of the user may fit comfortably within the indentation 122.

In some embodiments, the edge(s) of the indentation 122 may form the shape of a "U". In such embodiments, the indentation 122 may have three regions. A first region of the indentation 122 is the portion of the indentation 122 that is closest to the bottom portion of the U-shaped edge. The first region of the indentation 122 may be configured to contact and/or conform to a bottom portion of the back of the user's head. A second region of the indentation 122 is the portion of the indentation 122 that is closest to the right-side portion of the U-shaped edge. A third region of the indentation 122 is the portion of the indentation 122 that is closest to the left-side portion of the U-shaped edge. The second and third regions of the indentation 122 may be configured to contact and/or conform to the side portions of the back of the user's head.

In some embodiments, the depth throughout the indentation 122 may be uniform. In some other embodiments, the depth throughout the indentation 122 may be non-uniform. Because the shape of the back of the user's head is round (e.g., has a curve/curvature), non-uniformity with respect to the depth of different regions of the indentation may increase the surface area in contact with (and therefore providing comfort to) the head of the user. In the embodiments where the depth throughout the indentation 122 is non-uniform, the depth of the first region of the indentation 122 (e.g., the region of the indentation 122 that is closest to the bottom portion of the U-shaped edge) may be less than the depth of the second region and/or third region of the indentation 122 (e.g., the region(s) of the indentation 122 that is/are closest to the right side and/or left side of the U-shaped edge).

The bottom portion 118 of the headrest 112 may be wedge-shaped. The wedged-shaped bottom portion 118 may contact the shoulder(s) of the user. More specifically, the wedge-shaped bottom portion 118 may fit in the space between the back of the user's shoulder(s) and a seat against which the user may be leaning. In some embodiments, the wedge-shaped bottom portion 118 has no curves. For example, the bottom portion has only straight edges. In some other embodiments, the bottom portion 118 has one or more curvatures. As such, the edges of the bottom portion 118 have one or more curves. For example, a first portion of the edges of the bottom portion 118 may form a convex curve, and a second portion of the edges of the bottom portion 118 may form a concave curve. The first and second portions of the edges of the bottom portion 118 may be connected together or may be separated by a non-curved portion.

The headrest 112 may be configured to attach to the seat. In an aspect, the headrest 112 provides a means for accommodating the head of the user and attaching to the seat (e.g., the means for accommodating and attaching). The headrest straps 124'/124" may be connected to the headrest 112 and configured to adjustably fasten the headrest 112 to the seat. In an aspect, the headrest straps 124'/124" may provide a means for adjustably fastening the means for accommodating and attaching to the seat. The connection(s) between the headrest straps 124'/124" and the headrest 112 may be adjustable along any side portion 116 of the headrest 112. The headrest straps 124'/124" may include a first portion 124' and a second portion 124" that are detachably connected together using a buckle 126. The headrest straps 124'/124" may adjustably fasten the headrest 112 to the seat by wrapping around the seat.

The headrest 112 may be connected to an eye cover 102. The eye cover 102 may be configured to cover the eyes of the user to block at least some light from the eyes of the user. In an aspect, the eye cover 102 may provide a means for covering the eyes of the user. The headrest 112 and the eye cover 102 may be connected by eye cover straps 108. The eye cover straps 108 may be configured to adjustably fasten the eye cover 102 to the eyes of the user. The connection(s) 110 between the eye cover straps 108 and the headrest 112 may be adjustable along any side portion 116 of the headrest 112. For example, the connection(s) 110 between the eye cover straps 108 and the headrest 112 may be at a lower region of the side portion 116 of the headrest as is shown in the example illustrated in FIG. 1.

The eye cover 102 may have a perimeter region 106 and a central region 104. The material forming the perimeter region 106 may be different from the material forming the central region 104. For example, the material forming the central region 104 may have a higher density, thereby providing improved light-blocking, relative to the material forming the perimeter region 106. As another example, the material forming the perimeter region 106 may have some elastic properties, thereby creating a tight seal between the user's face and the eye cover 102 to provide improved light-blocking, relative to the material forming the central region 104.

The various aspects described herein may have various dimensions. In some embodiments, the vertical height of the headrest 112 (e.g. the distance from the top of the top portion 114 of the headrest 112 to the bottom of the wedge-shaped bottom portion 118 of the headrest 112) is approximately 30 inches. In some configurations, the maximum horizontal depth (e.g., the distance from the front portion 120 of the headrest 112 to the back portion of the headrest) is approximately 3 inches. However, one of ordinary skill in the art will appreciate that various aspects of the present disclosure may have alternative dimensions without deviating from the scope of the present disclosure.

Figure 2:
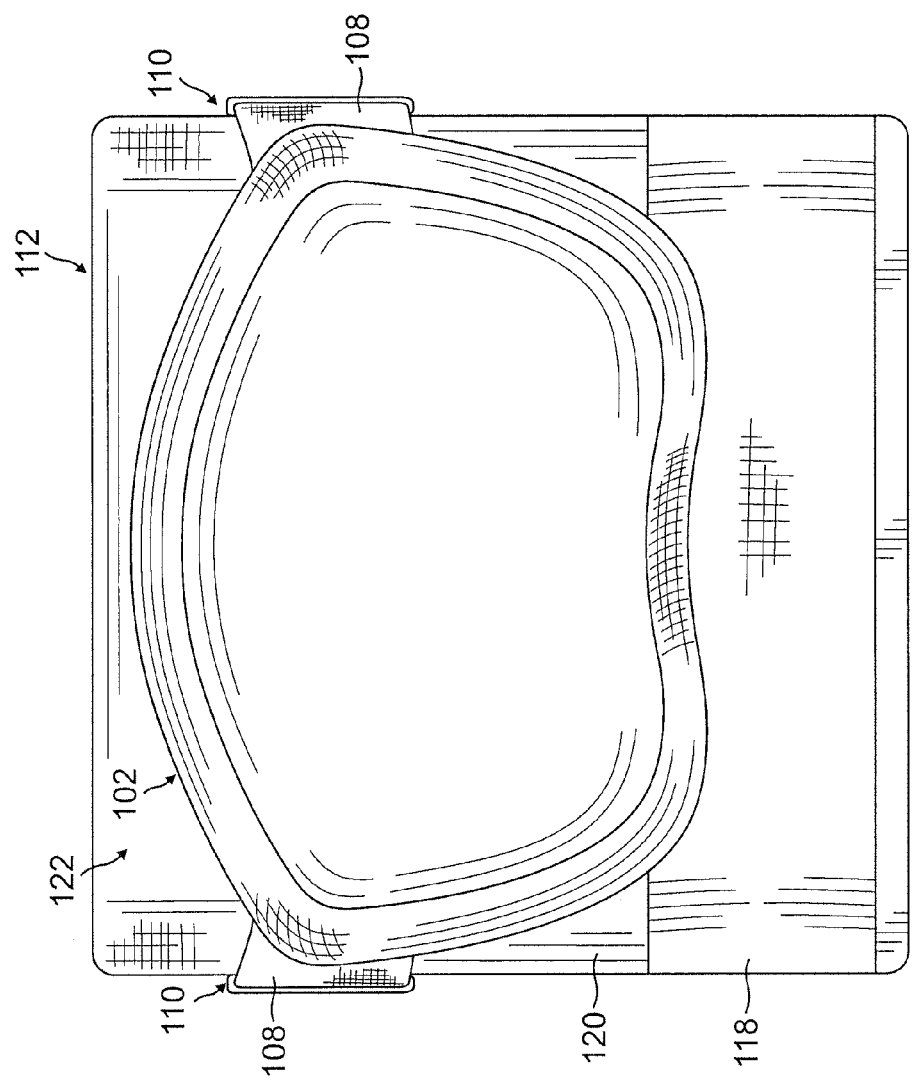
FIG. 2 is a diagram illustrating a front perspective view of the example attachable headrest with eye cover.

FIG. 2 is a diagram illustrating a front perspective view of the example attachable headrest 112 with eye cover 102. As described supra, the eye cover 102 is connected to the headrest 112. The connection(s) 110 between the eye cover straps 108 and the headrest 112 may be adjustable. For example, the connection(s) 110 may be adjusted such that the connection(s) 110 exist at any part of the side of the headrest 112. For example, the connection(s) 110 between the eye cover straps 108 and the headrest 112 may be located above and/or below the location where the connection(s) 110 is/are illustrated in FIG. 2. The wedged-shaped bottom portion 118 may contact the shoulder(s) of the user such that the wedge-shaped portion fits in the space between the back of the user's shoulder(s) and a seat against which the user may be leaning.

Figure 3:
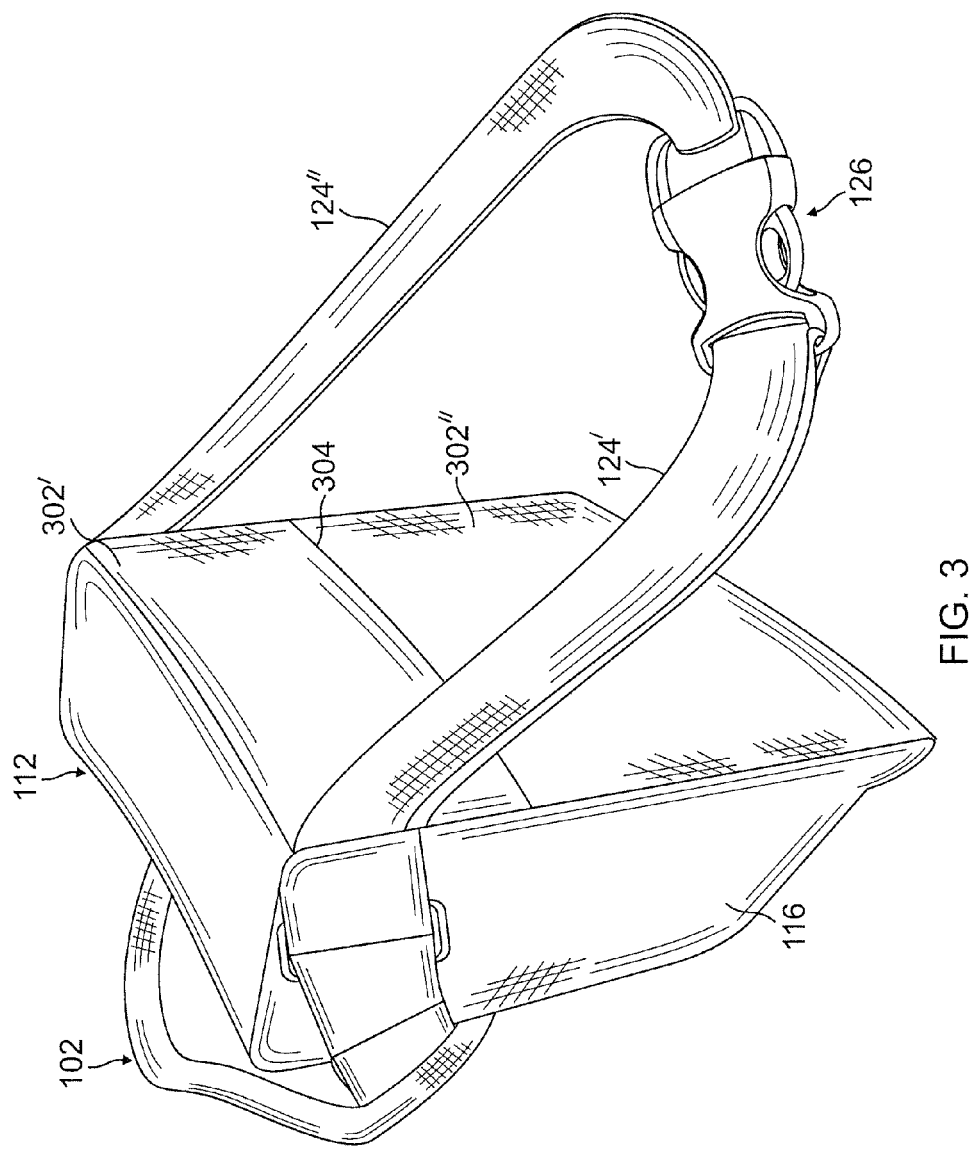
FIG. 3 is a diagram illustrating a rear perspective view of the example attachable headrest with eye cover.

FIG. 3 is a diagram illustrating a rear perspective view of the example attachable headrest 112 with eye cover 102. As described supra, the headrest straps 124'/124" may be connected to the headrest 112 and configured to adjustably fasten the headrest 112 to the seat. The connection(s) between the headrest straps 124'/124" and the headrest 112 may be adjustable along any side portion 116 of the headrest 112. The headrest straps 124'/124" may include a first portion 124' and a second portion 124" that are detachably connected together using a buckle 126. The headrest straps 124'/124" may adjustably fasten the headrest 112 to the seat by wrapping around the seat.

The headrest 112 may have a cover that may be removed using an opening in the rear portion of the headrest 112. For example, the top portion 302' of the rear material of the headrest 112 may detachably connect to the bottom portion 302" of the rear material of the headrest 112. The connection 304 between the top portion 302' and the bottom portion 302" may be a zipper, buttons, or simply a crease. The cover may be removed for washing and subsequently placed back on the headrest 112. Alternatively, the cover may be replaced or interchanged with other covers for style or color preferences. For example, different covers may have different colors or styles, and an individual may wish to replace the cover of the headrest 112 to suit their style preferences.

Figure 4:
FIG. 4 is a diagram illustrating a side perspective view of an example application of the example attachable headrest with eye cover.

FIG. 4 is a diagram illustrating a side perspective view of an example application of the example attachable headrest 112 with eye cover 102. The headrest straps 124 wrap around the seat 404 to hold the headrest 112 in a fixed position. The user is sitting upright in the seat 404. The head 402 of the user is resting against the headrest 112. The headrest 112 is positioned between the head 402 of the user and the seat 404. The shoulder of the user is contacting the wedge-shaped bottom portion of the headrest 112. The eyes of the user are covered by the eye cover 102. The eye cover straps 108 connect the eye cover 102 to the headrest 112. In addition, the eye cover straps 108 can be tightened such that the head 402 of the user is comfortably braced to the headrest 112, and the headrest 112 is attached to the seat 404 by the headrest straps 124. Accordingly, the headrest 112 and eye cover 102 may be configured to limit movement of the head 402 of the user. More specifically, the movement of the head 402 of the user is limited when the headrest 112 is fastened to the seat 404 and the eye cover 102 is fastened over eyes of the user.

Figure 5:
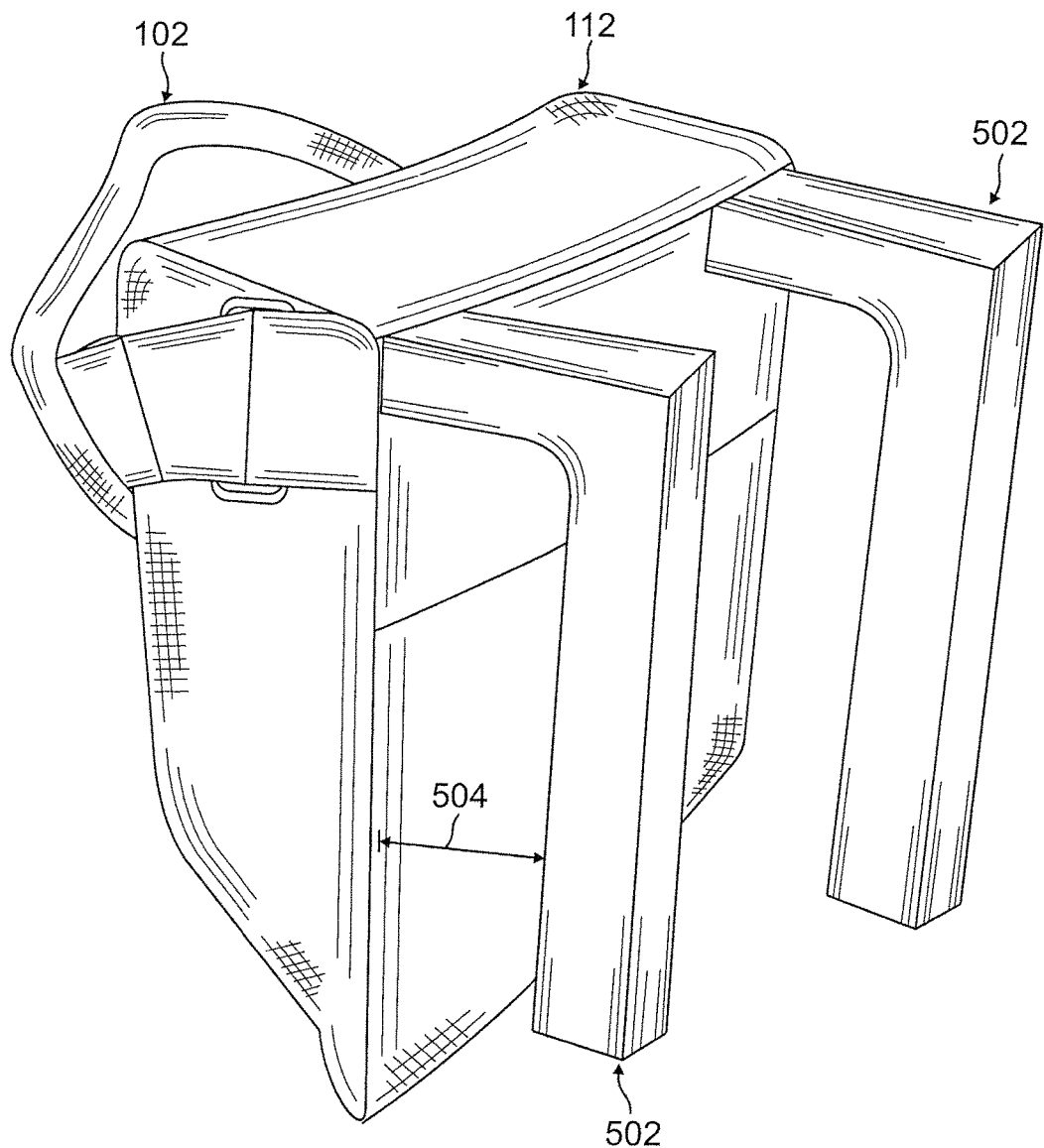
FIG. 5 is a diagram illustrating a rear perspective view of another example of an attachable headrest with eye cover.

FIG. 5 is a diagram illustrating a rear perspective view of another example of an attachable headrest 112 with eye cover 102. Because some portions of this example of the attachable headrest 112 with eye cover 102 are similar to the example described supra with respect to FIGS. 1-4, such portions will not be repeated infra. In the example illustrated in FIG. 5, rather than using headrest straps 124 (see FIG. 4), the headrest 112 may be attached to the seat using arms 502 that are configured to secure to a top portion of the seat. In an aspect, the arms 502 may provide a means for latching the means for accommodating and attaching to the top portion of the seat. The distance 504 between the rear portion of the headrest 112 and the arms 502 may correspond to the depth of the seat to which the headrest 112 may be attached. In some configurations, the arms 502 may be configured to be adjustable such that the distance 504 between the arms 502 and the rear portion of the headrest 112 accommodates different seats. In an aspect, the means for latching is adjustable to accommodate seats of different dimensions.

The foregoing description is provided to enable any person skilled in the art to fully understand the scope of the invention. Modifications to various aspects disclosed herein will be readily apparent to those skilled in the art. Accordingly, the scope of the claims will not be limited to the various exemplary embodiments provided herein.

Reference to an element in the singular is not intended to mean "one and only one" unless specifically stated as such; instead, reference to an element in the singular shall mean "one or more." Unless specifically stated otherwise, the term "some" refers to one or more. A claim that recites at least one of a combination of elements (e.g., "at least one of A, B, and C") refers to one or more of the recited elements (e.g., A, or B, or C, or any combination thereof).

No claim element is to be construed under the provisions of 35 U.S.C. § 112, sixth paragraph, unless the element is expressly recited using the phrase "means for" or, in the case of a method claim, the element is recited using the phrase "step for."

Thus, the claims are not intended to be limited to the various aspects of this disclosure, but are to be accorded the full scope consistent with the language of the claims. All structural and functional equivalents to the various components of the exemplary embodiments described throughout this disclosure that are known to those of ordinary skill in the art are expressly incorporated herein by reference and are intended to be encompassed by the claims.

What is claimed is:

1. An apparatus, comprising:
a headrest configured with an indentation shaped substantially similar to at least a back portion of a head of a user, the indentation configured to accommodate the head of the user by contacting the back portion of the head of the user when in use, and configured to be attached to a seat;
headrest straps connected to the headrest and configured to adjustably fasten the headrest to the seat; and
an eye cover connected to the headrest and configured to cover eyes of the user, the eye cover having a perimeter region and a central region, the material forming the perimeter region being a different material from the material forming the central region, the material forming the central region having a higher density,
wherein the headrest and eye cover are collectively configured to limit movement of the head of the user, the indentation comprising a semi-spherical cavity substantially opposite the eye and wherein the headrest comprises a wedged portion that contacts a shoulder of the user when in use, and wherein a strap of the eye cover is connected to the headrest on a side of the headrest substantially perpendicular to a side of the headrest having the indentation and along a corner opposite the indentation, a connection of the strap of the eye cover and a connection of the headrest straps are substantially co-located.

2. The apparatus of claim 1, wherein the headrest straps adjustably fasten the headrest to the seat by wrapping around the seat.

3. The apparatus of claim 1, wherein connections between the headrest straps and the headrest are adjustable along any side region of the headrest.

4. The apparatus of claim 1, wherein the headrest straps comprise a first portion and a second portion that are detachably connected together using a buckle.

5. The apparatus of claim 1, wherein the headrest and the eye cover are connected by eye cover straps configured to adjustably fasten the eye cover to the head of the user for covering the eyes of the user.

6. The apparatus of claim 5, wherein connections between the eye cover straps and the headrest are adjustable along any side region of the headrest.

7. The apparatus of claim 5, wherein the eye cover straps attach to an edge portion of the headrest at a first headrest attachment point and a second headrest attachment point, the first headrest attachment point and the second headrest attachment point located on opposite sides of the edge portion, the semi-spherical cavity located between the first headrest attachment point and the second headrest attachment point, at least a portion of the semi-spherical cavity located within a plane of the first headrest attachment point and the second headrest attachment point, a portion of the semi-spherical cavity substantially perpendicular to the plane of the first headrest attachment point and the second headrest attachment point.

8. The apparatus of claim 1, further comprising:
one or more rigid arms configured to attach the headrest to a top portion of the seat, wherein the arms are adjustable to accommodate seats of different dimensions.

9. An apparatus, comprising:
means for accommodating a head of a user including an indentation shaped substantially similar to at least a back portion of the head of the user by contacting the back portion of the head of the user when in use;
means for attaching the apparatus to a seat;
means for adjustably fastening the means for accommodating and the means for attaching; and
means for covering eyes of the user, wherein the means for covering eyes is connected to the means for accommodating, the means for covering eyes of the user having a perimeter region and a central region, the material forming the perimeter region being a different material from the material forming the central region, the material forming the central region having a higher density,
wherein the means for accommodating, the means for attaching, and the means for covering eyes are collectively configured to restrain movement of the head of the user, the indentation comprising a semispherical cavity substantially opposite the means for covering eyes of the user and wherein the means for accommodating a head of a user comprises a wedged portion that contacts a shoulder of the user when in use, and wherein a strap of the means for covering eyes of the user is connected to the means for accommodating a head of a user on a side of the means for accommodating a head of a user substantially perpendicular to a side of the means for accommodating a head of a user having the indentation and along a corner opposite the indentation, a connection of the strap of the means for covering eyes of the user and a connection of the means for adjustably fastening are substantially co-located.

10. The apparatus of claim 9, wherein the means for adjustably fastening are configured to wrap around the seat.

11. The apparatus of claim 9, wherein connections between the means for adjustably fastening and the means for accommodating are adjustable along any side region of the means for accommodating.

12. The apparatus of claim 9, wherein the means for adjustably fastening comprise a first portion and a second portion that are detachably connected together using a buckle.

13. The apparatus of claim 9, wherein the means for covering and the means for accommodating are connected by eye cover straps configured to adjustably fasten the means for covering to the head of the user.

14. The apparatus of claim 13, wherein connections between the eye cover straps and the means for accommodating are adjustable along any side region of the means for accommodating and the means for attaching.

15. The apparatus of claim 9, further comprising:
means for latching the means for accommodating to a top portion of the seat, wherein the means for latching includes adjustable rigid arms to accommodate seats of different dimensions.

16. The apparatus of claim 1, wherein the eye cover and the indentation are substantially opposite each other along a plane substantially perpendicular to the headrest when the headrest is in use by the user, the plane located above a neck of the user and substantially perpendicular to an axis of the neck of the user when the headrest is in use by the user, the eye cover comprising a single piece.

17. The apparatus of claim 1, wherein the wedged portion forms a concave curve.

18. The apparatus of claim 1, wherein the indentation forms a U shaped area having first, second, and third regions, the first region of the U shaped area of the indentation configured to contact and conform to a bottom portion of the head of the user, the second region of the U shaped area of the indentation closest to a right-side portion of the U-shaped edge and the third region of the U shaped area of the indentation closest to the left-side portion of the U-shaped edge, the second and third regions configured to contact and conform to the side portions of the head of the user, top portions of the second and third regions adjacent the strap.

19. The apparatus of claim 1, wherein a bottom of the apparatus comprises a bottom portion of the wedge portion that is separate from any other part of the apparatus such that the wedge may fit in the space between a back of the user's shoulders and a seat against which the user is leaning when the apparatus is in use.

* * * * *